United States Patent
Kang et al.

(10) Patent No.: US 12,364,991 B2
(45) Date of Patent: Jul. 22, 2025

(54) FLUID SEPARATION SYSTEM AND METHOD WHICH USES MAGNETIC PARTICLES

(71) Applicant: UNIST(ULSAN NATIONAL INSTITUTE OF SCIENCE AND TECHNOLOGY), Ulsan (KR)

(72) Inventors: Joo Hun Kang, Ulsan (KR); Se Yong Kwon, Ulsan (KR); Ji Eung Oh, Ulsan (KR)

(73) Assignee: UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 1103 days.

(21) Appl. No.: 16/785,396

(22) Filed: Feb. 7, 2020

(65) Prior Publication Data

US 2020/0261922 A1    Aug. 20, 2020

Related U.S. Application Data

(63) Continuation-in-part of application No. PCT/KR2018/008964, filed on Aug. 7, 2018.

(30) Foreign Application Priority Data

Aug. 7, 2017   (KR) ..................... 10-2017-0099610

(51) Int. Cl.
| | | |
|---|---|---|
| *B03C 1/01* | (2006.01) | |
| *B01L 3/00* | (2006.01) | |
| *B03C 1/033* | (2006.01) | |
| *B03C 1/28* | (2006.01) | |
| *C12N 15/10* | (2006.01) | |
| *G01N 33/543* | (2006.01) | |

(52) U.S. Cl.
CPC ............ *B03C 1/01* (2013.01); *B01L 3/50273* (2013.01); *B01L 3/502761* (2013.01); *B03C 1/0332* (2013.01); *B03C 1/0335* (2013.01); *B03C 1/288* (2013.01); *C12N 15/1013* (2013.01); *G01N 33/54326* (2013.01); *B01L 2200/0668* (2013.01); *B01L 2400/043* (2013.01); *B03C 2201/18* (2013.01); *B03C 2201/26* (2013.01)

(58) Field of Classification Search
CPC .. B03C 1/32; B03C 1/01; B03C 1/035; B03C 1/0335; B03C 1/0332; B03C 1/288; B03C 2201/18; B03C 2201/26; B01L 3/50273; B01L 3/502761; B01L 2200/0668; B01L 2400/043; B01L 3/00; B01L 2200/0652; G01N 33/54326; G01N 35/00; C12N 15/1013

See application file for complete search history.

(56) References Cited

U.S. PATENT DOCUMENTS

| | | | |
|---|---|---|---|
| 2006/0223178 A1 | 10/2006 | Barber et al. | |
| 2007/0207548 A1 | 9/2007 | Blankenstein | |
| 2009/0047297 A1 | 2/2009 | Kim et al. | |
| 2009/0078614 A1* | 3/2009 | Varghese | B03C 1/0332 |
| | | | 209/636 |
| 2009/0088336 A1* | 4/2009 | Burd | G01N 35/00732 |
| | | | 506/9 |
| 2009/0220932 A1* | 9/2009 | Ingber | G01N 15/1433 |
| | | | 435/308.1 |
| 2011/0262933 A1* | 10/2011 | Dryga | C12Q 1/6806 |
| | | | 435/7.1 |
| 2012/0080360 A1* | 4/2012 | Stone | B03C 1/01 |
| | | | 210/695 |
| 2012/0122731 A1* | 5/2012 | Soh | B03C 1/30 |
| | | | 506/12 |
| 2016/0327550 A1 | 11/2016 | Dryga et al. | |

FOREIGN PATENT DOCUMENTS

| | | |
|---|---|---|
| JP | 2002-503334 | 1/2002 |
| KR | 10-0809866 | 3/2008 |
| KR | 10-1071449 | 10/2011 |
| KR | 10-1099290 | 12/2011 |
| KR | 10-2015-0058955 | 5/2015 |

OTHER PUBLICATIONS

Robert, D et al. Cell sorting by endocytotic capacity in a microfluidic magnetophoresis device. Lab Chip. 2011. 11: 1902-1910. (Year: 2011).*
Schaller, J et al. "Blood Components." in: Human Blood Plasma Proteins: Structure and Function. (Chichester, England, John Wiley & Sons, 2008), pp. 7-16. (Year: 2008).*
Kang, JH et al. An extracorporeal blood-cleansing device for sepsis therapy. Nature Medicine. 2014. 20(10): 1211-1216. (Year: 2014).*
International Search Report and Written Opinion for PCT/KR2018/008964, mailed Nov. 14, 2018 (English translation of International Search Report).
Office Action for Korean Application No. 10-2021-0008296, mailed Feb. 9, 2021 (w/English translation).
Office Action for Korean Application No. 10-2018-0092059, mailed Oct. 7, 2020 (w/English translation).
Shen, Fengshan, "Magnetophoretic Label-Free Cell Separation Using Paramagnetic Solution in a Microchannel," Thesis, Korea Advanced Institute of Science and Technology (Jun. 2010).

* cited by examiner

*Primary Examiner* — Adam Weidner
*Assistant Examiner* — Susan E. Fernandez
(74) *Attorney, Agent, or Firm* — Klarquist Sparkman, LLP

(57) ABSTRACT

One embodiment relates to a system and method by which the magnetic susceptibility of a fluid is changed to separate the fluid according to differences in magnetic susceptibility. According to one embodiment, a fluid separation system and method can efficiently separate materials contained in a fluid according to magnetic susceptibility, without damage such as hemolysis or without changes in the types or concentrations of marker proteins in plasma.

7 Claims, 17 Drawing Sheets

FLUID SEPARATION SYSTEM AND METHOD WHICH USES MAGNETIC PARTICLES

CROSS REFERENCE TO RELATED APPLICATIONS

This is a continuation-in-part of International Application No. PCT/KR2018/008964, filed Aug. 7, 2018, which in turn claims priority to Korean Patent Application No. 10-2017-0099610, filed Aug. 7, 2017, which applications are incorporated herein in their entireties.

TECHNICAL FIELD

The present invention relates to a system for separating materials from a fluid using magnetic particles, and a method using the same.

BACKGROUND ART

As technologies for separating plasma from whole blood, technologies using centrifugation, filter separation, or microfluidic chips are available. However, when these separation technologies are applied to plasma separation, the separated plasma may have poor purity, and hemolysis of blood cells often occurs due to the application of excessive physical stimulation of the blood cells. Once the hemolysis of blood cells occurs, hemoglobin, potassium ions, proteins, nucleic acids, or the like present in the cells may spread into the plasma. This may affect the analysis of blood components, leading to incorrect test results.

In microfluidic control technologies which have recently been developed, plasma is separated by inertia and the interaction of blood cells with microstructures, and therefore less hemolysis occurs than in centrifugation or filter separation. However, there are also drawbacks such as poor purity and low yield of the separated plasma, and very slow separation speeds. As an additional drawback, since it is difficult to use whole blood as they are, it is necessary to dilute the blood with buffer before use.

Therefore, there is a need for the development of a fluid separation technology for rapidly separating plasma with high purity, without causing the hemolysis of blood cells.

DESCRIPTION OF EMBODIMENTS

Technical Problem

According to an aspect, there is provided a fluid separation method including: mixing a fluid and magnetic particles to change magnetic susceptibility of the fluid; injecting the fluid into a channel having one or more inlets and two or more outlets; passing the fluid through a domain where a magnetic field is created; and separating materials from the fluid according to differences in magnetic susceptibility.

According to another aspect, there is provided a fluid separation system including: a channel in which fluid is able to flow; one or more inlets; two or more outlets; magnetic particles for imparting paramagnetism to the fluid; a magnet (or electromagnet) for creating a magnetic field in the channel, wherein fluid flows to pass through a domain where the magnetic field is created, to thereby separate and discharge the materials contained in the fluid according to differences in paramagnetism or magnetic susceptibility, through the two or more outlets.

Another aspect provides a fluid separation and target material detection system including: a channel in which fluid is able to flow; one or more inlets; one or more outlets; magnetic particles for imparting paramagnetism to the fluid; and a magnet for creating a magnetic field in the channel, wherein a material capable of binding to the target material is immobilized on at least a portion of the wall inside the channel adjacent to a magnet, and the fluid containing the magnetic particles is guided to flow through the channel to a domain in which a magnetic field is created, and thus, by using the difference in magnetic susceptibility of the fluid and one or more materials other than the target material included in the fluid, the contact between materials other than the target material and the material capable of binding to the target material is prevented.

Another aspect provides a fluid separation and target material detection method, including changing magnetic susceptibility of a fluid containing a target material with magnetic particles; injecting the resultant fluid into a channel having one or more inlets and one or more outlets; passing the fluid through a domain where a magnetic field is created; allowing the target material binding to the material capable of binding to the target material immobilized on at least a portion of the wall of the channel inside the channel near a magnet for creating a magnetic field inside the channel; and separating materials included in the fluid according to the difference in magnetic susceptibility to be discharged through to flow through one or more outlets.

Solution to Problem

Hereinafter, embodiments of a fluid separation device and a fluid separation method using the same will be described with reference to the drawings. In the drawings, like reference numerals refer to like elements throughout and the sizes or thicknesses of elements are exaggerated for clarity.

According to an aspect, there is provided a fluid separation method including: mixing a fluid and magnetic particles to change magnetic susceptibility of the fluid; injecting the fluid into a channel having one or more inlets and two or more outlets; passing the fluid through a domain where a magnetic field is created; and separating materials from the fluid according to difference in magnetic susceptibility.

According to another aspect, there is provided a fluid separation device or system including: a channel in which fluid is able to flow; one or more inlets; two or more outlets; magnetic particles for imparting paramagnetism to the fluid; a magnet for creating a magnetic field in the channel, wherein fluid flows through the channel to pass through a domain where the magnetic field is created, to thereby separate and discharge the materials contained in the fluid according to differences in paramagnetism or magnetic susceptibility, through the two or more outlets.

FIG. 1 illustrates a fluid separation method according to an aspect of the present invention. Referring to FIG. 1, a mixture of a fluid 1 and magnetic particles 2 may be injected into a first inlet 110a which is located on a side of a channel 100. The injected fluid 1 may pass through a magnetic field domain formed by a first magnet 200a along the channel 100. The materials in the fluid may be separated according to magnetic susceptibility into a relatively strong paramagnetic or ferrormagnetic portion, which is to flow through a first outlet 120a located relatively close to the first magnet, and a relatively weak paramagnetic or diamagnetic portion, which is to flow through a second outlet 120b located relatively far away from the first magnet. Accordingly, fluid for separation 5 contained in the fluid 1 may be separated according to magnetic susceptibility.

The width and height of the channel may be properly controlled by a person skilled in the art according to the type of the fluid or the purpose of separation. For example, to separate plasma from blood (or whole blood), the channel may have a width of about 0.001 mm to about 10 mm and a height of about 1 µm to about 100 mm. The flow rate of the fluid flowing in the channel may be property controlled by a person skilled in the art according to the type of the fluid or the purpose of separation. For example, to separate plasma from whole blood, the flow rate may be about 0.1 µL/min to about 10 mL/min.

The magnetic particles 2 may include paramagnetic particles. Paramagnetism means a property of weak magnetization, which occurs only when a magnetic field is present, in the direction of the magnetic field. The magnetic particles may be those manufactured using a known method, or those sold commercially. The diameter of the magnetic particles is not specifically limited. The magnetic particles may be magnetic nanoparticles having a small diameter, for example, may have a diameter of about 1 nm to about 200 nm. A magnetic material of the magnetic particles may be a magnetic metal or an oxide of a magnetic metal (for example, a magnetic oxide such as iron oxide). The magnetic metal may consist of at least one metal selected from iron-group metal elements (Fe, Ni, Co), rare earth elements (La, Ce, Pr, Nd, Pm, Sm, Eu, Gd, Tb, Dy, Ho, Er, Tm, Yb, Lu), money metal elements (Cu, Ag, Au), zinc-group elements (Zn, Cd, Hg), aluminum-group elements (Al, Ga, In, Tl), alkaline earth metal elements (Ca, Sr, Ba, Ra), and platinum-group elements (Pt, Pd, or the like), or an alloy thereof. In an embodiment, the magnetic particles may include at least one type selected from, for example, the group consisting of Co, Mn, Fe, Ni, Gd, Mo, MM'$_2$O$_4$, and M$_p$O$_q$. Here, M and M' may each independently be Co, Fe, Ni, Mn, Zn, Gd, or Cr, 0<p≤≤3, and 0<q≤≤5.

The magnetic particles 2 may include a detection material attached thereto, the detection material capable of specifically binding to a target material contained in the fluid. The target material may be, for example, any compounds, nucleic acids, proteins, or peptides. The detection material may be an antibody, a fragment of an antibody, an aptamer, a nucleic acid, a peptide, a protein, or any compound which are capable of specifically binding to the target material. For example, when the target material is a biomarker of a specific disease, a person skilled in the art may prepare an antibody capable of binding to the biomarker, or commercially purchase a material known to bind to the biomarker, and then attach the prepared antibody or the purchased material to the magnetic particles.

The term "biomarker" may refer to any biological indicator which can objectively measure and evaluate normal biological processes, disease progression, and the effectiveness of a drug with respect to a treatment method. The biomarker may include genes, gene mutations, nucleic acids, proteins, peptides, bacteria, viruses, cells, or levels of cell-derived materials, including exosomes, cytokines, or the like.

FIG. 2 illustrates a fluid separation method according to another aspect of the present invention. Referring to FIG. 2, a fluid may be separated using a channel having two or more inlets and three or more outlets. An additional mixing step may be omitted by injecting different materials into the two or more inlets, respectively. Two or more magnets having different magnetism may be arranged underneath the channel to create magnetic fields having different intensities according to domains of the channel. By creating magnetic fields having different intensities for different domains of the channel in this way, it is possible to more precisely separate materials contained in a fluid according to magnetic susceptibility using a plurality of outlets.

A magnetic structure 150 may be located in the outlet. As the magnetic structure 150 has a stronger magnetic field than the surroundings, the magnetic particles 2 may be separated by the magnetic field. Accordingly, the magnetic particles 2 included in the separated fluid may be removed, as necessary. The magnetic structure may include nickel, iron, ferrite, a rear earth metal, or an alloy thereof, or a metal structure which can be commonly magnetized. Or, the magnetic structure may include an electromagnet structure which generates a magnetic force by electromagnetic induction.

When a detection material for detecting a target material is attached to the magnetic particles 2, the target material may be detected from the magnetic particles separated with the magnetic structure. The detecting of the target material may be achieved using a known technology by a person skilled in the art. For example, when the target material is a nucleic acid, the target material may be detected using real-time polymerase chain reaction (RT-PCR), RNase protection assay (RPA), Northern blotting, or a DNA chip. When the target material is a protein, the target material may be detected using Western blotting, enzyme linked immunosorbent assay (ELISA), radioimmunoassay (RIA), radio-immunodiffusion, Ouchterlony immunodiffusion, rocket immunoelectrophoresis, immunohistochemical staining, immunoprecipitation assay, complement fixation assay, fluorescence activated cell sorting (FACs) analysis, or a protein chip.

FIG. 3 illustrates a method of separating whole blood, according to another aspect of the present invention. Referring to FIG. 3, the whole blood injected into the channel may be allowed to flow through a domain in which a magnetic field is created. In general, plasma is relatively strongly paramagnetic, white blood cells are diamagnetic, and red blood cells are weakly paramagnetic. Due to such difference, all the blood cells may be pushed towards regions of weaker magnetic field and be separated from the plasma. The separated blood may be discharged through a plurality of outlets. Accordingly, it is possible to continuously separate the plasma depending on the position of the outlets, the intensity of the magnetic field, or the discharge time.

A detection material capable of specifically binding to a target material contained in blood may be attached to the magnetic particles. As illustrated in FIG. 3, antibodies which specifically bind to a biomarker in the blood may be attached to the magnetic particles. After the plasma is separated from the whole blood, the magnetic particles may be separated from the plasma using a nickel (Ni) structure. Then, the biomarker in the plasma may be detected using a secondary antibody labeled with a fluorescent material. In such a manner, plasma separation and biomarker detection may be performed at the same time.

In one embodiment, the magnetic particles may enter into the material contained in the fluid. The material included in the fluid may be a cell or a microorganism, and specifically, may be a bacteria, a virus, or the like. In one embodiment, the cell or the microorganism may be a cell or a microorganism in which at least one of a cell membrane and a cell wall is damaged, and accordingly, in the cell or the microorganism, the permeability of at least one of the cell membrane and the cell wall is higher than that of a normal cell or a microorganism, or the cell or the microorganism in which at least one of the cell membrane and the cell wall is damaged may be included in normal cells or normal microorganisms, and accordingly, the magnetic particles may enter into the cell or the microorganism in which at least one of the cell membrane and the cell wall is highly permeable or at least one of the cell membrane and the cell wall is damaged. In one embodiment, when magnetic particles enter into the cell or the microorganism, paramagnetic particles that have a concentration similar to that in the surrounding fluid, may exist inside the cell or the microorganism, and therefore, in the magnetic field, cells or microorganisms having weak paramagnetic or diamagnetic properties may be pushed away from the magnet, but the cell or the microorganism in which at least one of a cell membrane and a cell wall is damaged, may hardly be pushed away from the magnet, thereby leaving nucleic acids of more cells or microorganisms inside the fluid. Accordingly, in one embodiment, the fluid separation system, the fluid separation method, or the target material detection method may be used to isolate the cell or the microorganism in which at least one of a cell membrane and a cell wall is highly permeable than normal cells or normal microorganisms, or isolate the cell or microorganism in which at least one of a cell membrane and a cell wall is damaged, or diagnose an infectious disease. The infectious disease may be sepsis and the like.

Another aspect provides a fluid separation and target material detection system including: a channel in which fluid is able to flow; one or more inlets; one or more outlets; magnetic particles for imparting paramagnetism to the fluid; and a magnet for creating a magnetic field in the channel, wherein a material capable of binding to the target material is immobilized on at least a portion of the wall inside the channel adjacent to the magnet, and the fluid containing the magnetic particles is guided to flow through the channel to a domain in which a magnetic field is created, and thus, by using the difference in magnetic susceptibility between the fluid and one or more materials other than the target material included in the fluid, the contact between materials other than the target material and the material capable of biding to the target material is prevented.

When the fluid is injected into the channel and the magnet is placed on one side of the channel where the material capable of binding to the target material is immobilized, the blood cell is pushed away from the surface of the channel on which the material capable of binding to the target material is immobilized, and the target material is brought into contact the material capable of binding to the target material immobilized on the channel surface and thus, the immunoassay may be performed without the interruption of the blood cell.

In one embodiment, the material capable of binding to the target material may be beads.

The beads may be those manufactured using a known method, or those sold commercially. The diameter of the beads is not particularly limited, but may be from about 10 nm to about 1 mm, and the material constituting the beads is not particularly limited.

The material capable of binding to the target material may be immobilized on the wall inside the channel by using a physical or chemical method. The physical method may be to form an engraved pattern on the wall inside the channel and to fix the material thereon. For example, the engraved pattern may be a pattern selected from a polygon, such as a circle, a triangle, a rectangle, a rhombus, a honeycomb, and a wave shape, a straight line or a curve, or a combination thereof. When the engraved pattern is a polygon, the diameter thereof or the length of one side thereof may be about 1 nm to about 1 mm.

When the blood containing magnetic particles is injected into the channel and the magnet is placed on one side of the channel where the material capable of binding to the target material is immobilized, blood cells are pushed away from the surface of the channel on which the material capable of binding to the target material is immobilized, and only plasma components contact the surface of the channel on which the material capable of binding to the target material is immobilized, and thus, the immunoassay may be performed without the interruption of the blood cells.

From among the terms or elements described in connection with the fluid separation and the target material detection system, those described in connection with the method of separating the fluid separation system or fluid are understood the same as described in connection with the fluid separation system or the fluid separation method.

Another aspect provides a fluid separation and target material detection method, including changing the magnetic susceptibility of a fluid containing a target material with magnetic particles; injecting the resultant fluid into a channel having one or more inlets and one or more outlets; passing the fluid through a domain where a magnetic field is created; allowing the target material binding to the material capable of binding to the target material immobilized on at least a portion of the wall of the channel inside the channel near a magnet for creating a magnetic field inside the channel; and separating materials included in the fluid according to the difference in magnetic susceptibility to be discharged through one or more outlets.

In one embodiment, the material capable of binding to the target material may be beads.

In one embodiment, the method may further include binding, to a material labeled with fluorescence, the target material that binds to the material capable of binding to the target material.

The material labeled with fluorescence may be a fluorescence-labeled antibody. For example, fluorescence-labeled antibody capable of binding to a target material is bound to a target material bound to immobilized beads, or an antibody (primary antibody) capable of binding to a target material is bound to a target material bound to immobilized beads, and then a fluorescence-labeled antibody (second antibody) is bound thereto.

From among the terms or elements described in connection with the fluid separation and the target material detection method, those described in connection with the method of separating the fluid separation system or fluid, or a target material detection method are understood the same as described in connection with the fluid separation system, the fluid separation method, or the target material detection method.

Advantageous Effects of Disclosure

According to the embodiments of the present invention, using the fluid separation system and method, materials contained in a fluid can be efficiently separated according to magnetic susceptibility without damage such as hemolysis or without changes in types or concentrations of marker proteins in plasma.

BRIEF DESCRIPTION OF DRAWINGS

FIG. 10A is a schematic side view of an apparatus for detecting proteins in plasma using whole blood without centrifugation;

FIG. 10B is an image of fluorescence attached on secondary antibodies bound to beads which have been treated with primary and secondary antibodies after the mixture including blood and 4 ng/mL PSA is allow to flow in a channel with the beads, with which anti-PSA antibody binds, located at the bottom thereof (Whole blood, top), an image of fluorescence attached on secondary antibodies bound to beads which have been treated with primary and secondary antibodies after blood including 10 nm paramagnetic particles (SPIONs) is mixed with 4 ng/mL PSA and the mixture is allowed to flow in the channel including a magnet located on the surface of the channel on which beads are immobilized (Whole blood supplemented with SPIONs, middle), and an image of fluorescence attached on secondary antibodies bound to beads which have been treated with primary and secondary antibodies after 4 ng/mL PSA is mixed with blood and then plasma obtained by centrifugation is allowed to flow in the channel (Plasma, bottom);

FIG. 10C shows results obtained by mixing various concentrations of PSA with blood using the methods.

FIG. 11A is a schematic view of an apparatus for detecting a nucleic acid in plasma using whole blood without centrifugation;

FIG. 11B shows diagrams showing that when 10 nm paramagnetic particles (SPIONs) are mixed with bacteria-containing blood, in the case of bacteria in which a cell membrane and a cell wall are damaged, 10 nm-size paramagnetic particles (SPIONs) enter into the bacteria cell through the damaged cell membrane and cell wall, and thus, blood cells showing paramagnetic or diamagnetic properties in the magnetic field are pushed away from the magnet, and in the case of bacteria in which a cell membrane and a cell wall are damaged, the concentrations of paramagnetic particles contained inside/outside liquid of cells are similar to each other and thus, the cells are not effectively pushed away.

FIG. 11C shows the case in which plasma is obtained using the channel according to the present disclosure (left), and the case in which although a nucleic acid attached on a bacteria in which a cell membrane and a cell wall are damaged and a nucleic acid released from bacteria existing in plasma may be obtained, when plasma is obtained by centrifugation (right), a nucleic acid attached on bacteria is separated together with blood cells from plasma in a centrifugation process, and thus, only a nucleic acid released from the bacterial body remains in the plasma.

FIG. 11D shows quantitative results obtained by a real-time polymerase chain reaction of bacterial nucleic acid in a plasma obtained by each of a method according to the present disclosure in which the bacteria of which the cell membrane is destroyed is added to blood (graph: Diamagnetic) and a centrifugation method (graph: Centrifugation)

MODE OF DISCLOSURE

One or more embodiments of the present disclosure will now be described in detail with reference to the following examples. However, these examples are only for illustrative purposes and are not intended to limit the scope of the one or more embodiments of the present disclosure.

EXAMPLE 1

Plasma Separation using Paramagnetic Particles

The whole blood taken from 8-week-old Wistar rats was mixed with magnetic nanoparticles (carboxylated iron oxide, 10 nm, Ocean NanoTech, US, paramagnetic nanoparticles, 1 mg/mL), and then injected into a channel having a width of about 1 mm and a height of about 100 μm. A permanent magnet was arranged about 500 μm away from the bottom of the channel to create a magnetic field. A negative pressure was applied to an outlet portion of the channel with a micropump to allow the whole blood to flow (2 μL/min).

Figure 1:
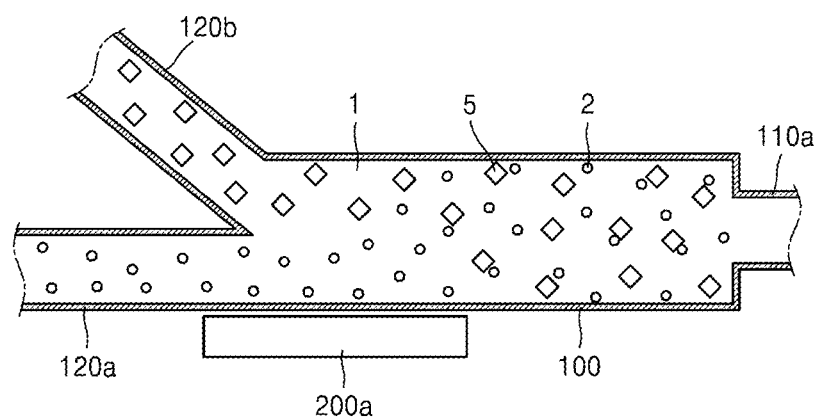
FIG. 1 illustrates a method of separating materials in a fluid according to magnetic susceptibility.
Figure 2:
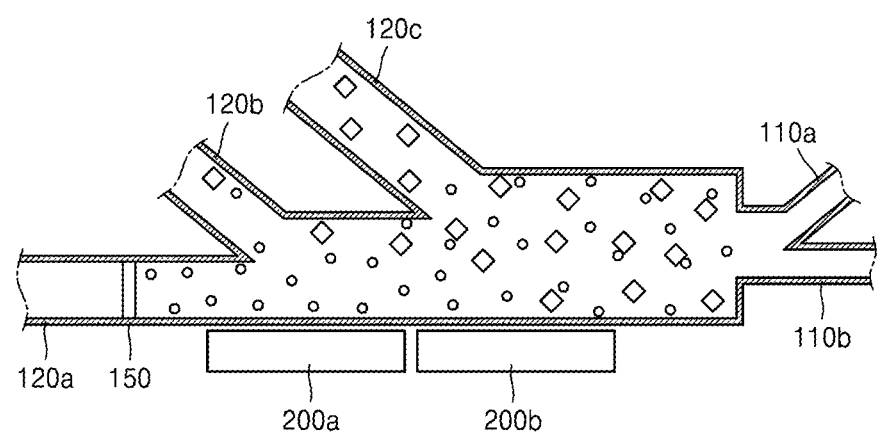
FIG. 2 illustrates a method of separating materials in a fluid according to magnetic susceptibility using a channel having two or more inlets and three or more outlets.
Figure 3:
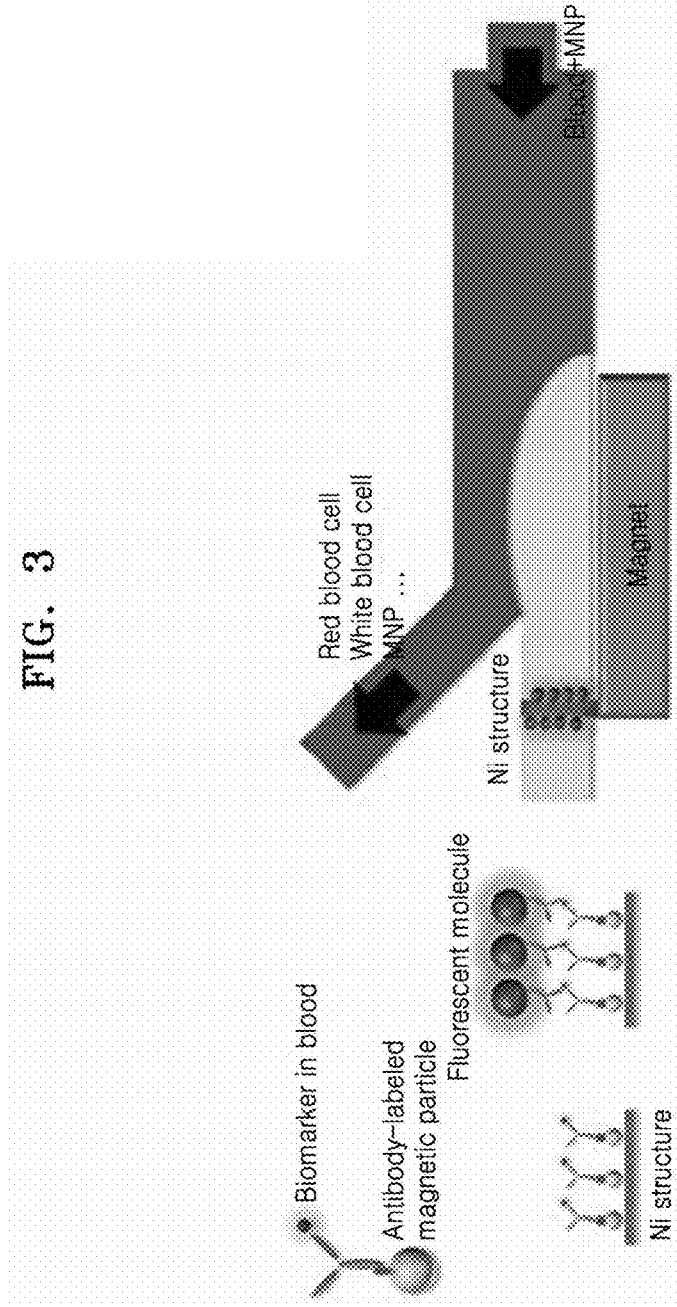
FIG. 3 illustrates a method of separating blood cells according to magnetic susceptibility and attaching antibodies to magnetic particles to detect a biomarker included in the blood.
Figure 4:
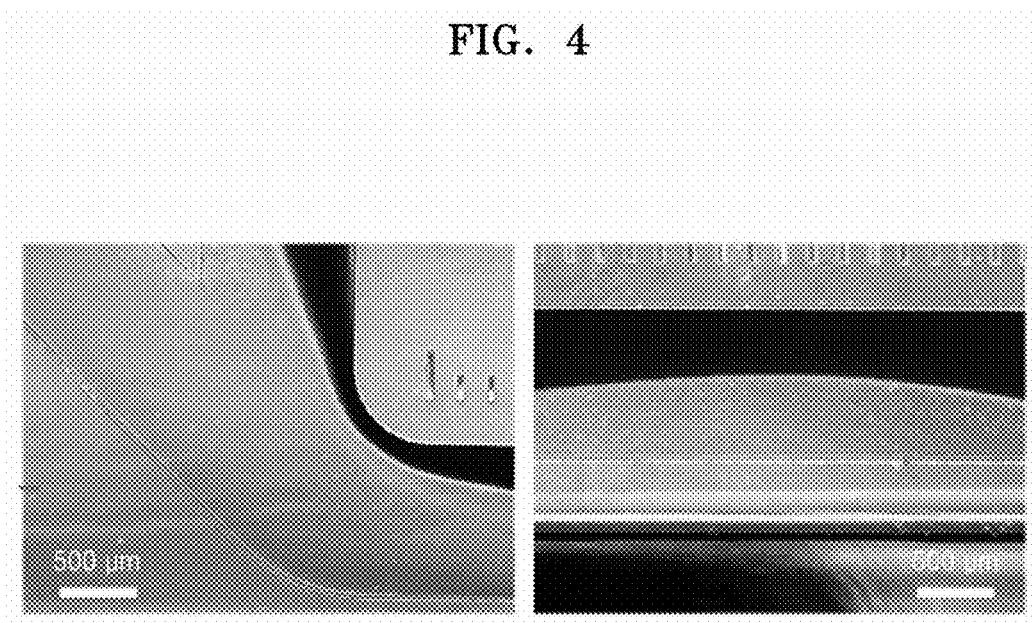
FIG. 4 shows images of plasma separated from blood using magnetic susceptibility differences according to an embodiment.

As a result, as shown in FIG. 4, the separation of the plasma from the whole blood was clearly observed. The dark red portion is the area where blood cells such as red blood cells and white blood cells are concentrated, and the remaining transparent portion is the plasma.

In addition, as a result of experiments with a channel having a width of about 5 mm and a height of about 700 μm in which the location of a magnetic field creation domain is varied, it was found that plasma can be separated at 5 μL/min, indicating that the plasma separation rate can be increased by widening the channel.

EXAMPLE 2

Purity Measurement on Plasma Separated using Paramagnetic Particles

Figure 5:
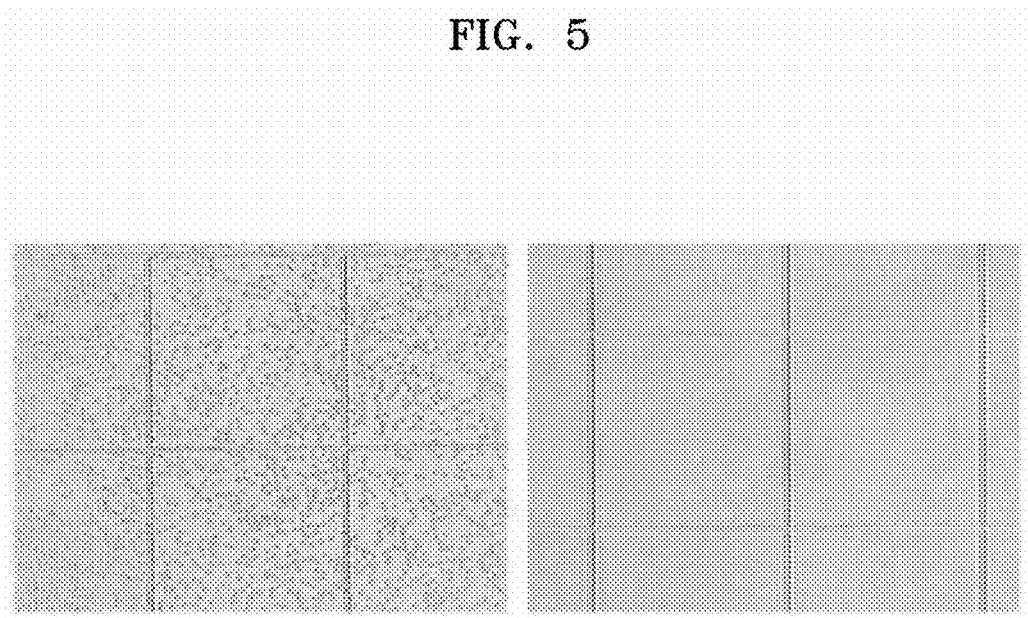
FIG. 5 illustrates an image (left) of a 1:200 dilution of blood and an image (right) of separated plasma according to an embodiment.

The plasma separated in Example 1 was subjected to purity measurement. A 1:200 dilution of the blood and the plasma separated in Example 1 were comparatively observed using a microscope (Olympus CKX53, 20× Object lens). As shown in FIG. 5, a large number of blood cells which were observed in the diluted blood were not observed in the plasma separated in Example 1.

Figure 6:
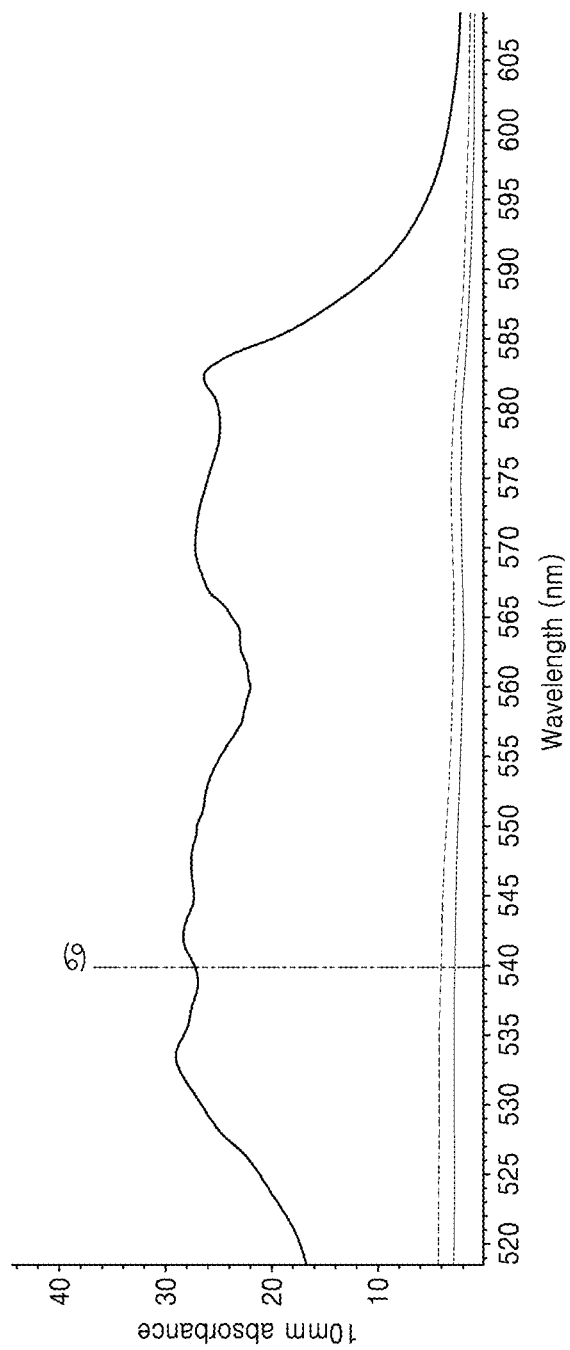
FIG. 6 illustrates the results of absorbance measurement of hemoglobin in separated plasma according to an embodiment.

FIG. 6 illustrates the results of absorbance measurement of hemoglobin in the separated plasma using a NanoDrop (ThermoFisher Scientific, USA). The value at a wavelength of 540 nm wavelength is interpreted as a hemoglobin absorbance value. In FIG. 6, the yellow line at the bottom represents the absorbance of the plasma separated in Example 1, which was found to have a hemoglobin level lower than that of the plasma obtained by centrifugation (the blue middle line) or the plasma obtained by hemolysis of the blood cells with Triton-X(X-100) (1%) and then centrifugation (the red uppermost line).

As a result of calculating a hemolysis percentage on the basis of the data of FIG. 6, the hemolysis percentage was about 5.76%, indicating less hemolysis than with existing centrifugation technology. According to existing technologies, since plasma is separated from blood cells using pressure difference or size difference, hemolysis may occur easily. However, it was found that using difference in magnetic field density and paramagnetic materials may cause less hemolysis than in existing centrifugation, since the external force applied to cells is so weak as not to cause hemolysis.

EXAMPLE 3

Observation of Hemolysis in Plasma Separated using Paramagnetic Particles

Hemolysis refers to the destruction of red blood cells leading to dissolution of red blood cell contents in plasma, and is a cause of an incorrect test result in the diagnosis of a disease with plasma. Thus, in Example 1, the hemolysis of blood cells which may occur in the process of separation was observed.

In particular, to check a hemolysis rate of the plasma obtained using paramagnetic particles, absorbances of a positive control group, a negative control group, and the plasma obtained using paramagnetic particles were measured using a Nanodrop (ThermoFisher Scientific, USA). To prepare the positive control group, the blood taken from 8-week-old Wistar rats was mixed with 1% Triton X-100 (Sigma Aldrich) and then reacted at about 36° C. for about 30 minutes to hemolyze the blood cells. Subsequently, the resulting blood was centrifuged at about 4° C. at 500×g for about 13 minutes to obtain the supernatant, which was used as a sample of the positive control group. To prepare the negative control group, the blood taken from the rats was centrifuged at about 4° C. at 500×g for about 13 minutes to obtain the supernatant, which was used as the negative control group. Next, absorbances of the positive control group, the negative control group, and the plasma obtained using paramagnetic particles were measured using a Nanodrop (ThermoFisher Scientific, USA). The results are shown in FIGS. 7A-B.

Figure 7A:
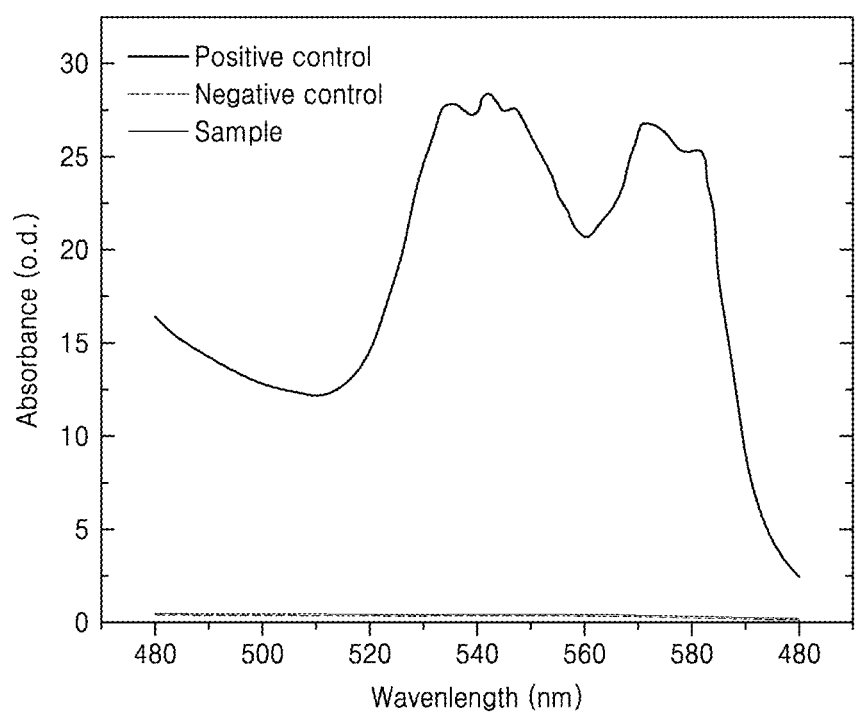
FIGS. 7A-B shows a graph (A) of absorbance measured at different wavelengths to observe hemolysis in separated plasma and a graph (B) of absorbance at 540 nm, according to an embodiment.
Figure 7B:
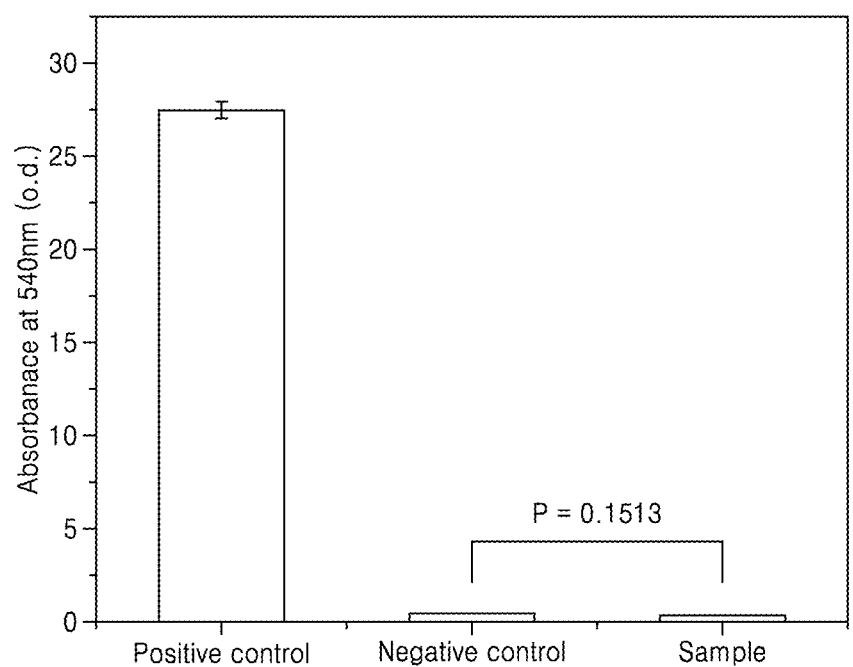

Referring to FIGS. 7A-B, it was found that the plasma obtained using paramagnetic particles had no difference in absorbance from the negative control group. This means that separating plasma using paramagnetic particles, according to an embodiment, does not cause hemolysis.

EXAMPLE 4

Verification of Protein Pattern in Plasma Separated using Paramagnetic Particles Proteins in plasma are available as a biomarker in the diagnosis of a disease. Accordingly, sodium dodecyl sulfate-polyacrylamide gel electrophoresis (SDS-PAGE) was used to verify whether the various proteins in plasma were well maintained after the separation of the plasma using paramagnetic particles. The plasma prepared as the negative control group in Example 3 was used, and the markers from Precision Plus Protein Dual Color Standards (BIO-RAD, CA, USA) were used, and it was identified that there were albumin (65 kDa), α1-globulin (44 kDa), α2-globulin (85 kDa), and fibrinogen (up to 340 kDa), which are plasma proteins. In particular, to perform SDS-PAGE, after 2× Laemmli Sample Buffer (available from BIO-RAD) and 2-mercaptoethanol (available from BIO-RAD) were mixed in a 9:1 ratio, the thus obtained mixture was mixed with the plasma in a 1:1 ratio. Then, the sample was immersed in boiling water for 3 minutes and then spun down. The Mini-PROTEAN® TGX™ Precast Gel (available from BIO-RAD) was assembled in an electrophoresis chamber (available from BIO-RAD). Next, after the electrophoresis chamber was filled with Tris/Glycine/SDS buffer (available from BIO-RAD), the sample and Precision Plus Protein Dual Color Standards (available from BIO-RAD) were added, and the electrophoresis system was operated. After staining with a Coomassie brilliant blue R-250 staining solution (BIO-RAD) for 2 to 3 hours, destaining was performed using a Coomassie Brilliant blue R-250 destaining solution (BIO-RAD). The results of the SDS-PAGE are shown in FIG. 8.

Figure 8:
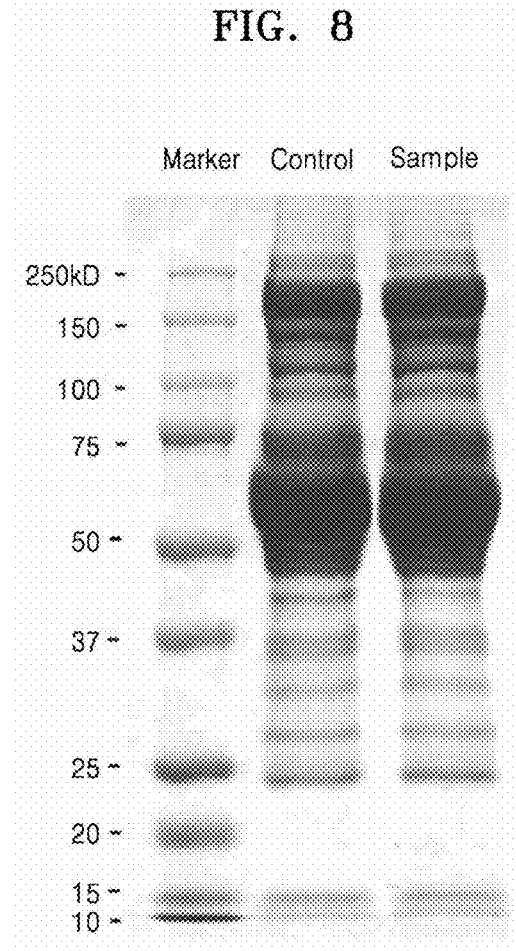
FIG. 8 is an image showing the results of sodium dodecyl sulfate-polyacrylamide gel electrophoresis (SDS-PAGE) performed to identify the types of proteins in separated plasma according to an embodiment.

Referring to FIG. 8, in the case of the plasma obtained using paramagnetic particles, it was found that the types of proteins in the plasma were not different from the protein in the plasma (Control) obtained by centrifugation. This means that separating plasma using paramagnetic particles, according to an embodiment, ensures that the various types of proteins in the plasma were well maintained after the separation.

EXAMPLE 5

Determination of Protein Concentration in Plasma Separated using Paramagnetic Particles Following Example 4, a bicinchoninic acid (BCA) protein assay was performed to determine the quantitative concentrations of the proteins in the plasma separated in Example 1.

In particular, the negative control group of Example 4 was used. The total protein concentrations in the plasma separated using paramagnetic particles and in the plasma of the negative control group were compared according to the manufacturer's instructions using a Pierce BCA Protein Assay Kit (ThermoFisher Scientific, USA). The results are shown in FIG. 9.

Figure 9:
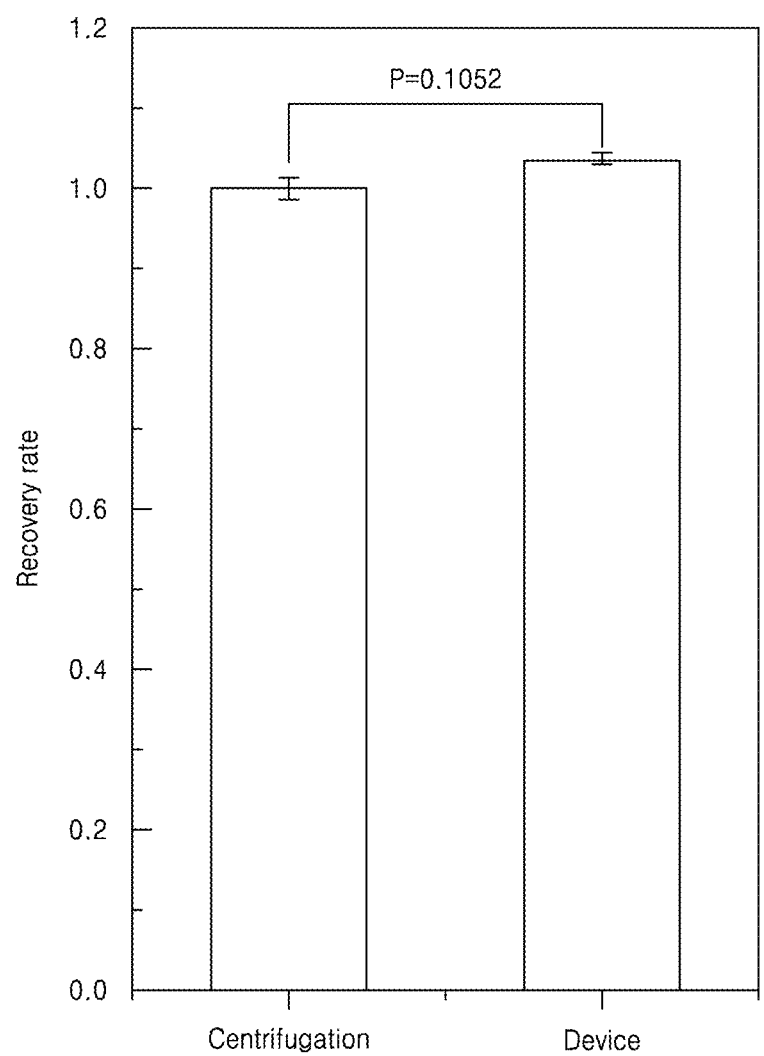
FIG. 9 is a graph illustrating the results of a bicinchoninic acid (BCA) protein assay performed to determine a protein concentration in separated plasma according to an embodiment ("Centrifugation" denotes a negative control group and "Device" denotes plasma separated using paramagnetic particles, according to an embodiment).

Referring to FIG. 9, the plasma separated using paramagnetic particles was found not to be different in total protein concentration from the plasma (control group) separated using centrifugation. Accordingly, it was found that in separating plasma using paramagnetic particles, according to an embodiment, the plasma may be separated well without loss in total protein, and with no influence on future assays using protein.

As a result, it was found that a plasma separation method using paramagnetic particles, according to an embodiment, ensures separation of the plasma without affecting the types and concentration of plasma proteins.

EXAMPLE 6

Target Protein Detection using Paramagnetic Particles

Anti-PSA antibody (Sino Biological, China) with biotin immobilized thereon was reacted with Streptavidin-immobilized magnetic beads (diameter of 18 μm; Spherotech, CA, USA) for 40 minutes at room temperature to prepare anti-PSA antibody immobilized magnetic beads. The magnetic beads were then washed three times with a washing buffer solution (tris-buffered saline with 0.05% Tween® 20 (TBST; Biosesang, Korea)), and then, reacted with biotin-polyethylene glycol (PEG; Nanocs, NY, USA) for 30 minutes at room temperature to prevent non-specific reactions. The beads were placed in a channel provided with a magnet located at the bottom surface thereof (0.1 mm×32.65 mm×0.08 mm; width×length×height) (FIGS. 10A-C) at a speed of 60 μL/h for 5 minutes to immobilize the beads on microgrooves (30 μm×30 μm; diameter×depth) at the bottom surface of the channel due to the magnet located at the bottom surface of the channel, and then, flushed with a washing buffer solution (TBST) at the speed of 200 μL/h for 6 minutes to remove the beads that are not immobilized. To the channel provided with the beads at the bottom surface thereof (the magnet is located at the bottom surface of the channel), blood including 10 nm-size paramagnetic particles and various concentrations of PSA (0, 2, 4, 10 ng/mL; BiosPacific, CA, USA) was provided at the speed of 3 μL/h for 45 minutes. In this process, the beads placed on the bottom surface of the channel only come into contact with plasma or the components contained in the plasma. Then, the washing buffer solution (TBST) was provided thereto to proceed with a washing process for 6 minutes at the speed of 200 μL/h. To detect the captured PSA, a primary antibody (anti-PSA rabbit IgG antibody; Abcam, UK) was provided at 30 μL/h for 30 minutes and a washing buffer solution was provided at the speed of 200 μL/h for 6 minutes. Fluorescence-labeled secondary antibodies capable of binding to the primary antibody (Alexa Fluor® 488 labeled goat anti rabbit IgG antibody; Abcam, UK) was provided thereto at the speed of 30 μL/h for 30 minutes. After washing with a washing buffer solution provided at the speed of 200 μL/h for 6 minutes, the intensity of fluorescence of 18 μm-size beads located on the bottom surface of the channel was measured by using a fluorescence microscope (Alexa Fluor® 488).

Figure 10A:
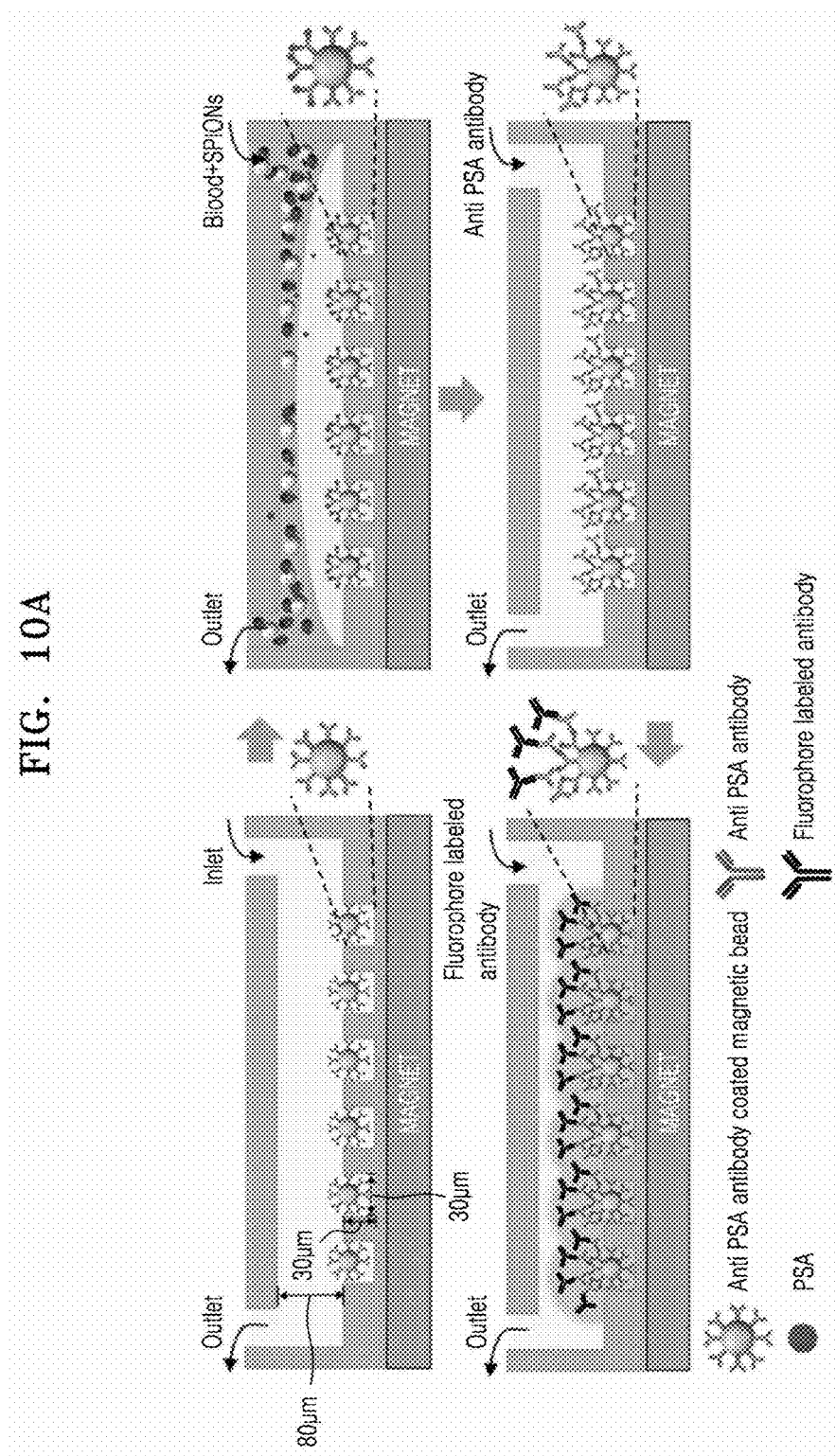
FIGS. 10A-C illustrates the target protein detection using paramagnetic particles.
Figure 10B:
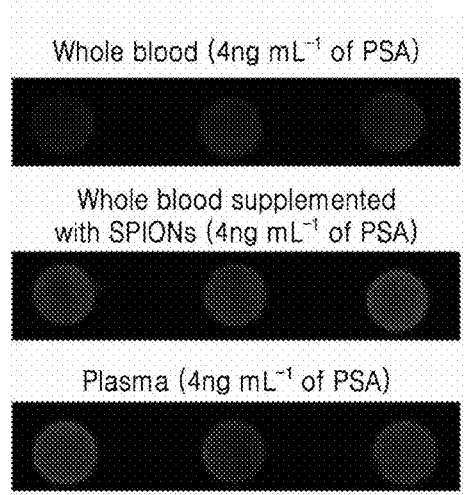

Like the results of FIG. 10B, when the present disclosure is applied to the channel-based immunoassay, even when plasma was not isolated prior to the assay, the same result as obtained with the case in which the isolated plasma was used for the assay may be obtained. Accordingly, it can be seen that even without expensive centrifugation devices and experts required therewith, the same level of measurements as obtainable in the conventional case may be obtained (see FIGS. 10B and 10C). The PSA detection limit of this system is 2.5 ng/mL, which is lower than the cut off value for diagnosing prostate cancer, which is 4 ng/mL. This shows that the present disclosure provides outstanding performance in providing information about the diagnosis of prostate cancer.

FIG. 10A is a schematic side view of an apparatus for detecting proteins in plasma using whole blood without centrifugation. The apparatus includes a channel in which blood flows (0.1 mm×32.65 mm×0.08 mm; width×length×height) and cylindrical microgrooves (30 μm×30 μm; diameter×depth) for immobilizing 18 μm-size beads on which antibodies are attached and which are located at the bottom surface of the channel (diameter of 18 μm). Anti-PSA antibodies are immobilized on the surfaces of the beads immobilized in the microgrooves, and proteins captured by antibodies (for example: prostate specific antigen (PSA)) are detected by the reaction occurring when other antibodies (primary antibody and fluorescence-labeled secondary antibodies) are sequentially provided into the channel after blood is provided to the channel, and fluorescent immunoassay.

As described above, when beads on which antibodies, which are capable of detecting proteins, attached, are placed at the bottom of the channel thereto and blood mixed with 10 nm paramagnetic particles (SPIONs) is provided thereto, due to the magnet at the bottom of the channel, blood cells are pushed away from the antibodies-attached beads, and thus, only plasma and components included in plasma are brought into contact with the antibodies-attached beads. This is because the magnetic susceptibility of the fluid (plasma) changes when the 10 nm-sized paramagnetic particles are mixed in the blood, so that the diamagnetic or weak paramagnetic blood cells are pushed away from a region having a strong magnetic field (magnet side, near the beads) to a region having a weak magnetic field (upwards the channel). Eventually, the same effect as obtainable when only plasma components are isolated and provided, may be obtained (FIG. 10B).

FIG. 10B is an image of fluorescence attached on secondary antibodies bound to beads which have been treated with primary and secondary antibodies after the mixture including blood and 4 ng/mL PSA is allow to flow in a channel with the beads, with which anti-PSA antibody bonds, located at the bottom thereof (Whole blood, top), an image of fluorescence attached on secondary antibodies bound to beads which have been treated with primary and secondary antibodies after the blood including 10 nm paramagnetic particles (SPIONs) is mixed with 4 ng/mL PSA and the mixture is allowed to flow in the channel (Whole blood supplemented with SPIONs, middle), and an image of fluorescence attached on secondary antibodies bound to beads which have been treated with primary and secondary antibodies after 4 ng/mL PSA is mixed with blood and then plasma obtained by centrifugation is allowed to flow in the channel (Plasma, bottom).

Figure 10C:
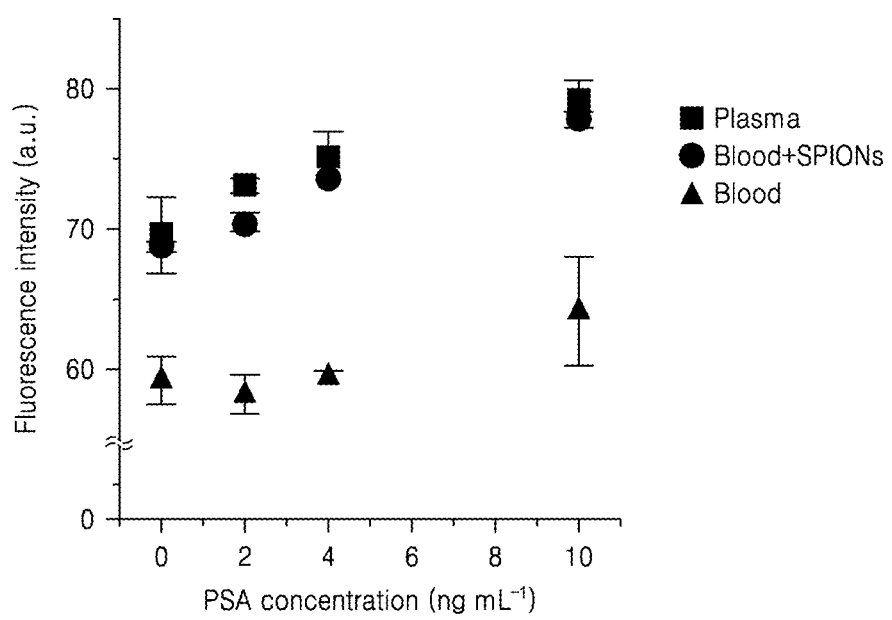

FIG. 10C shows results obtained by mixing various concentrations of PSA with blood using the methods. It was confirmed that the intensity of fluorescence obtained from blood supplemented with SPIONs (graph: Blood+SPIONs) was higher than the intensity of fluorescence obtained from blood without SPIONs (graph: Blood) at all concentrations of PSA, and all fluorescence values were similar to those obtained using plasma (graph: Plasma) obtained by centrifugation.

EXAMPLE 6

Nucleic Acid Separation using Paramagnetic Particles

After mixing the bacteria in which a cell membrane and a cell wall were artificially damaged in blood, plasma was obtained by centrifugation and the method according to the present invention, and then, through real-time polymerase chain reaction, the amount of the nucleic acid of bacteria obtained by centrifugation was compared with that obtained using the present disclosure.

$10^6$ CFU/mL E. coli K12 species (KCTC No.: 2223) was sonicated for 1 hour (50 W, 35° C.), and E. coli K12 was mixed with whole blood containing 10 nm-size paramagnetic particles at a ratio of 1(saline containing sonicated E. coli):10(whole blood containing paramagnetic particles). The resulting blood was allowed to flow into the channel and then, plasma was obtained through a plasma outlet (outlet 2) at the speed of 2 μL/min. The blood thus obtained was centrifuged (×800 g, 4° C., and 10 minutes) to obtain plasma from the supernatant. Using the DNeasy Blood & Tissue Kit (Qiagen, Germany), nucleic acids were extracted from the two plasmas according to the manufacturers instructions, and the nucleic acids were stored in a −20° C. freezer until the polymerase chain reaction. Nucleic acids were detected using a real-time polymerase chain reaction based on SYBR Green (LightCycler® 480 system (Roche, Switzerland) using E. coli K12 species-specific primer (Macrogen, Korea) and LightCycler® 480 SYBR Green I Master (Roche, Switzerland). Then, the amount of nucleic acid was analyzed using Delta crossing point ($C_p$) method.

Figure 11A:
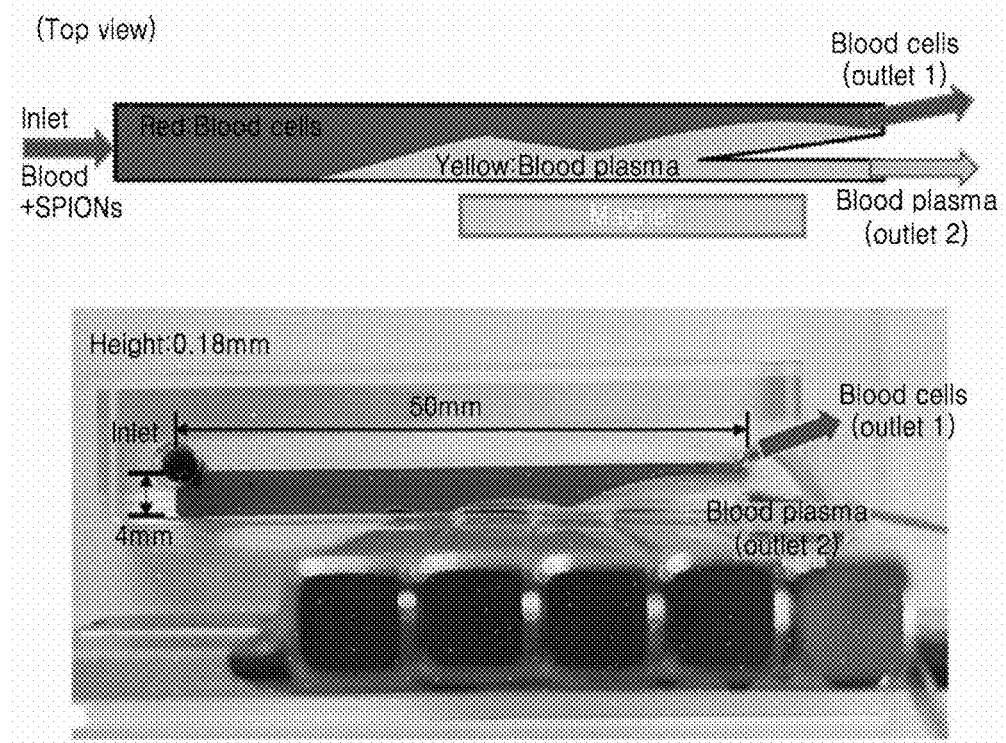
FIGS. 11A-D illustrates the nucleic acid separation using paramagnetic particles.
Figure 11B:
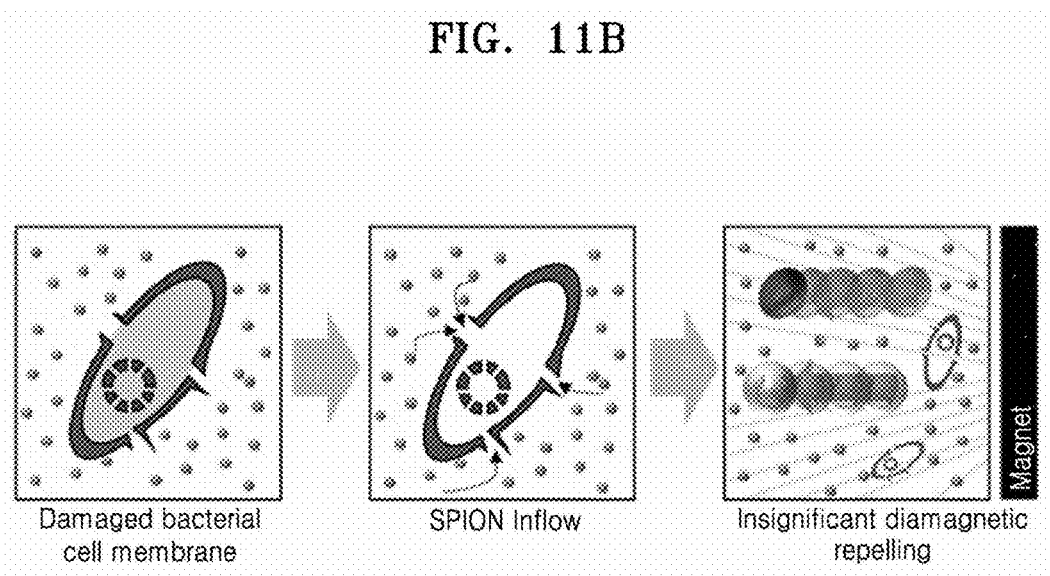
Figure 11C:
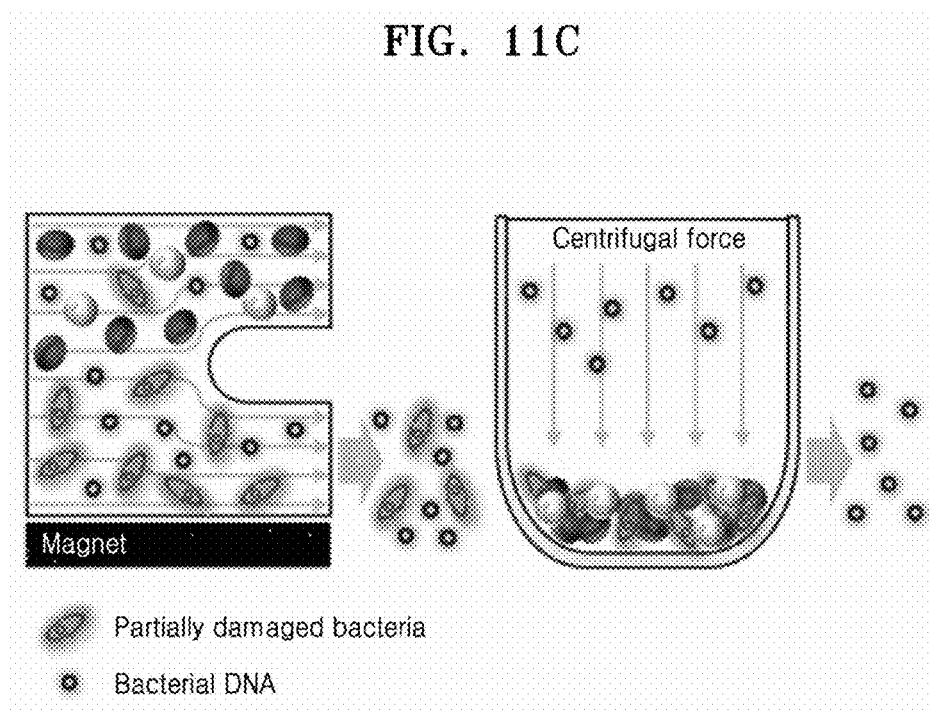
Figure 11D:
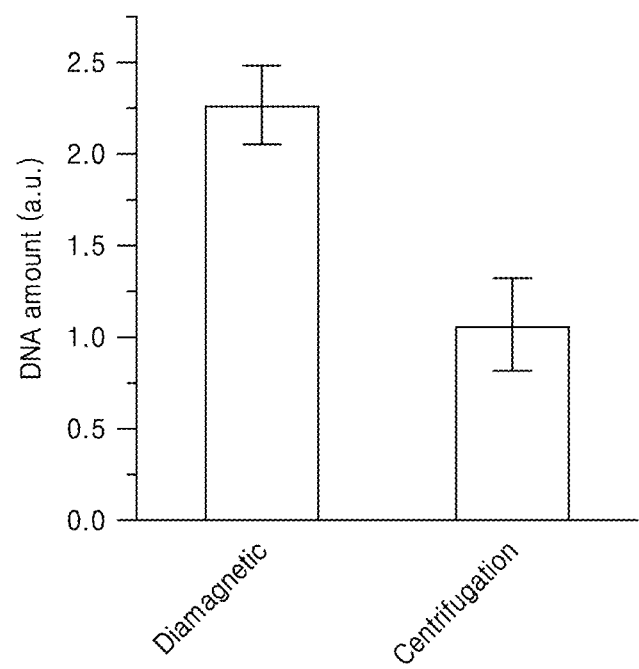

As shown in FIG. 11D, considering that the amount of E. coli nucleic acids obtained according to the present disclosure is about 2.3 times greater than the amount of nucleic acids obtained through centrifugation, it is expected that when the present disclosure is applied to the polymerase chain reaction, a faster and more accurate sepsis diagnostics can be developed.

FIG. 11A is a schematic view of an apparatus for detecting a nucleic acid in plasma using whole blood without centrifugation. The apparatus (channel size: 4 mm×50 mm×0.18 mm; width×length×height) includes an inlet blood enters, and outlet 1 through which blood cells are discharged and outlet 2 through which plasma is discharged.

FIG. 11B shows diagrams showing that when 10 nm paramagnetic particles (SPIONs) are mixed with bacteria-containing blood, in the case of bacteria in which a cell membrane and a cell wall are damaged, 10 nm-size paramagnetic particles (SPIONs) enter into the bacteria cell through the cell membrane and cell wall, and thus, blood cells showing paramagnetic or diamagnetic properties in the magnetic field are pushed away from the magnet, and in the case of bacteria in which a cell membrane and a cell wall are damaged, the concentrations of paramagnetic particles contained inside/outside liquid of cells are similar to each other and thus, the cells are not effectively pushed away.

FIG. 11C shows the case in which plasma is obtained using the channel according to the present disclosure (left), and the case in which although a nucleic acid attached on a bacteria in which a cell membrane and a cell wall are damaged and a nucleic acid released from bacteria existing in plasma may be obtained, when plasma is obtained by centrifugation (right), a nucleic acid attached on bacteria is separated together with blood cells from plasma in a centrifugation process, and thus, only a nucleic acid released from the bacterial body remains in the plasma.

FIG. 11D shows quantitative results obtained by a real-time polymerase chain reaction of bacterial nucleic acid in a plasma obtained by each of a method according to the present disclosure in which the bacteria of which the cell membrane and the cell wall is destroyed is added to blood (graph: Diamagnetic) and a centrifugation method (graph: Centrifugation) The amount of the bacterial nucleic acid obtained by the method of the present disclosure is about 2.3 times greater than the amount of the nucleic acid obtained by the centrifugation method.

The invention claimed is:

1. A fluid separation method comprising:
    mixing magnetic nanoparticles with a fluid containing a material to change magnetic susceptibility of the fluid;
    injecting the fluid into a channel having one or more inlets and two or more outlets;
    passing the fluid through a domain where a magnetic field is created; and
    separating the material from the fluid according to difference in magnetic susceptibility to be discharged through the two or more outlets,
    wherein the material is separated from the fluid by being pushed into a region of a weaker magnetic field, induced by a change in the fluid's magnetic susceptibility,
    wherein the magnetic nanoparticles enter into a cell or a microorganism contained in the fluid and,
    wherein the cell or the microorganism included in the fluid is a cell or a microorganism in which at least one of a cell membrane and a cell wall is damaged.

2. The fluid separation method of claim 1, wherein the fluid is blood containing blood cells and plasma, and the blood cells and the plasma are separated by the method.

3. The fluid separation method of claim 1, wherein the channel further comprises a magnetic structure for removing the magnetic nanoparticles.

4. The fluid separation method of claim 1, wherein the method is used to diagnose infectious disease.

5. A fluid separation and target material detection method comprising:
    mixing magnetic nanoparticles with a fluid containing a first material and a second material to change magnetic susceptibility of the fluid;
    injecting the fluid into a channel having one or more inlets and one or more outlets;
    passing the fluid through a domain where a magnetic field is created;
    allowing the target material contained in the second material to bind to a material capable of binding to the target material immobilized on at least a portion of the wall of the channel inside the channel near a magnet for creating a magnetic field inside the channel; and
    separating the first material included in the fluid according to difference in magnetic susceptibility to be discharged through one or more outlets,
    wherein the first material is separated from the fluid by being pushed into a region of a weaker magnetic field, induced by a change in the fluid's magnetic susceptibility.

6. The fluid separation and target material detection method of claim 5, wherein the material capable of binding to the target material is an antibody, a fragment of an antibody, an aptamer, a nucleic acid, a peptide, or a protein.

7. The fluid separation and target material detection method of claim 5, further comprising binding, to a material labeled with fluorescence, the target material that binds to the material capable of binding to the target material.

* * * * *